United States Patent
Johannaber

(10) Patent No.: US 10,004,516 B2
(45) Date of Patent: Jun. 26, 2018

(54) INTRAMEDULLARY RESECTION GUIDE AND METHODS

(71) Applicant: Zimmer, Inc., Warsaw, IN (US)

(72) Inventor: Kenneth D Johannaber, Rancho Murieta, CA (US)

(73) Assignee: Zimmer, Inc., Warsaw, IN (US)

( * ) Notice: Subject to any disclaimer, the term of this patent is extended or adjusted under 35 U.S.C. 154(b) by 723 days.

(21) Appl. No.: 13/789,087

(22) Filed: Mar. 7, 2013

(65) Prior Publication Data

US 2014/0257308 A1    Sep. 11, 2014

(51) Int. Cl.
| | |
|---|---|
| *A61B 17/90* | (2006.01) |
| *A61B 17/15* | (2006.01) |
| *A61B 17/64* | (2006.01) |
| *A61B 17/66* | (2006.01) |
| *A61B 90/11* | (2016.01) |
| *A61B 90/13* | (2016.01) |

(52) U.S. Cl.
CPC .......... *A61B 17/155* (2013.01); *A61B 17/154* (2013.01); *A61B 17/64* (2013.01); *A61B 17/66* (2013.01); *A61B 90/11* (2016.02); *A61B 90/13* (2016.02)

(58) Field of Classification Search
CPC ..... A61B 17/15; A61B 17/154; A61B 17/155; A61B 17/157; A61B 2019/467; F21V 21/096; F21V 21/0965
USPC ................... 606/87–88; 200/19.36, 61.45 M; 362/398
See application file for complete search history.

(56) References Cited

U.S. PATENT DOCUMENTS

| | | | |
|---|---|---|---|
| 7,726,974 B2 * | 6/2010 | Shah .................. | H05B 33/0803 439/40 |
| 8,021,368 B2 * | 9/2011 | Haines .................. | A61B 17/15 606/82 |

(Continued)

FOREIGN PATENT DOCUMENTS

| | | |
|---|---|---|
| EP | 1444957 A1 | 8/2004 |
| EP | 2964110 B1 | 12/2016 |

(Continued)

OTHER PUBLICATIONS

"International Application Serial No. PCT/US2014/018900, International Search Report dated May 23, 2014", 5 gs.

(Continued)

*Primary Examiner* — Tatiana Nobrega
*Assistant Examiner* — Jessica Weiss
(74) *Attorney, Agent, or Firm* — Schwegman Lundberg & Woessner, P.A.

(57) ABSTRACT

A bone cut positioning system and associated method are disclosed. The bone cut positioning system can include a positioning assembly. The positioning assembly can include a femoral attachment member configured to be fixed to a distal end of a femur, a light emitter mounting member configured to receive a light emitter, and a channel configured to receive a depth selector slide. Further, the positioning assembly can include a varus-valgus adjustment member configured to adjust a position of the positioning assembly relative to the femur to achieve a desired varus-valgus angle and a guide member removably coupled to the depth selector slide and configured to extend from the depth selector slide.

19 Claims, 10 Drawing Sheets

(56) References Cited

U.S. PATENT DOCUMENTS

| | | | | |
|---|---|---|---|---|
| 8,436,521 | B2* | 5/2013 | Shim | H01J 5/46 313/146 |
| 2005/0021039 | A1* | 1/2005 | Cusick | A61B 17/154 606/88 |
| 2005/0070897 | A1 | 3/2005 | Petersen | |
| 2006/0034091 | A1* | 2/2006 | Kovacik | F21L 14/023 362/398 |
| 2007/0043375 | A1 | 2/2007 | Anissian | |
| 2007/0073306 | A1* | 3/2007 | Lakin | A61B 17/155 606/87 |
| 2007/0173851 | A1* | 7/2007 | McMillen | A61B 17/1764 606/87 |
| 2008/0183178 | A1* | 7/2008 | Collazo | A61B 17/157 606/88 |
| 2008/0195109 | A1 | 8/2008 | Hunter et al. | |
| 2009/0234360 | A1* | 9/2009 | Alexander | A61B 17/15 606/88 |
| 2009/0239393 | A1* | 9/2009 | Shah | H05B 33/0803 439/40 |
| 2010/0063508 | A1* | 3/2010 | Borja | A61B 17/154 606/88 |
| 2010/0198275 | A1 | 8/2010 | Chana et al. | |
| 2011/0208093 | A1 | 8/2011 | Gross et al. | |
| 2012/0245589 | A1 | 9/2012 | Fisher et al. | |
| 2014/0257307 | A1 | 9/2014 | Johannaber | |
| 2016/0305641 | A1* | 10/2016 | Lin | F21V 23/005 |
| 2017/0100133 | A1 | 4/2017 | Johannaber | |

FOREIGN PATENT DOCUMENTS

| | | |
|---|---|---|
| WO | WO-2012176077 A1 | 12/2012 |
| WO | WO-2014137726 A1 | 9/2014 |
| WO | WO-2014138384 A1 | 9/2014 |

OTHER PUBLICATIONS

"International Application Serial No. PCT/US2014/018900, Written Opinion dated May 23, 2014", 6 pgs.

"International Application Serial No. PCT/US2014/021164, International Search Report dated May 13, 2014", 5 pgs.

"International Application Serial No. PCT/US2014/021164, Written Opinion dated May 13, 2014", 5 pgs.

"U.S. Appl. No. 13/789,049, Non Final Office Action dated Nov. 18, 2015", 13 pgs.

"International Application Serial No. PCT/US2014/018900, International Preliminary Report on Patentability dated Sep. 17, 2015", 8 pgs.

"International Application Serial No. PCT/US2014/021164, International Preliminary Report on Patentability dated Sep. 17, 2015", 7 pgs.

"U.S. Appl. No. 13/789,049, Final Office Action dated Jun. 16, 2016", 14 pgs.

"Application Serial No. 13/789,049, Response filed Feb. 18, 2016 to Non Final Office Action dated Nov. 18, 2015", 15 pgs.

"European Application Serial No. 14712819.3, Response filed May 9, 2016 to Communication pursuant to Rules 161(1) and 162 EPC dated Oct. 29, 2015", 12 pgs.

"U.S. Appl. No. 13/789,049, Response filed Aug. 16, 2016 to Final Office Action dated Jun. 16, 2016", 16 pgs.

"U.S. Appl. No. 13/789,049, Notice of Allowability dated Nov. 10, 2016", 4 pgs.

"U.S. Appl. No. 13/789,049, Notice of Allowance dated Oct. 24, 2016", 12 pgs.

"European Application Serial No. 14712950.6, Communication Pursuant to Article 94(3) EPC dated Nov. 7, 2016", 5 pgs.

"U.S. Appl. No. 13/789,049, Notice of Allowance dated Feb. 9, 2017", 7 pgs.

"U.S. Appl. No. 15/388,609, Preliminary Amendment Filed Dec. 28, 2016", 7 pgs.

"European Application Serial No. 14712950.6, Response filed Mar. 13, 2017 to Office Action dated Nov. 7, 2016", 9 pgs.

"U.S. Appl. No. 15/388,609, Response filed Feb. 2, 2018 to Non Final Office Action dated Nov. 3, 2017", 13 pgs.

"U.S. Appl. No. 13/789,049, Notice of Allowance dated Jan. 4, 2018", 7 pgs.

"U.S. Appl. No. 13/789,049, Notice of Allowance dated Sep. 12, 2017", 7 pgs.

"U.S. Appl. No. 15/388,609, Non Final Office Action dated Nov. 3, 2017", 17 pgs.

* cited by examiner

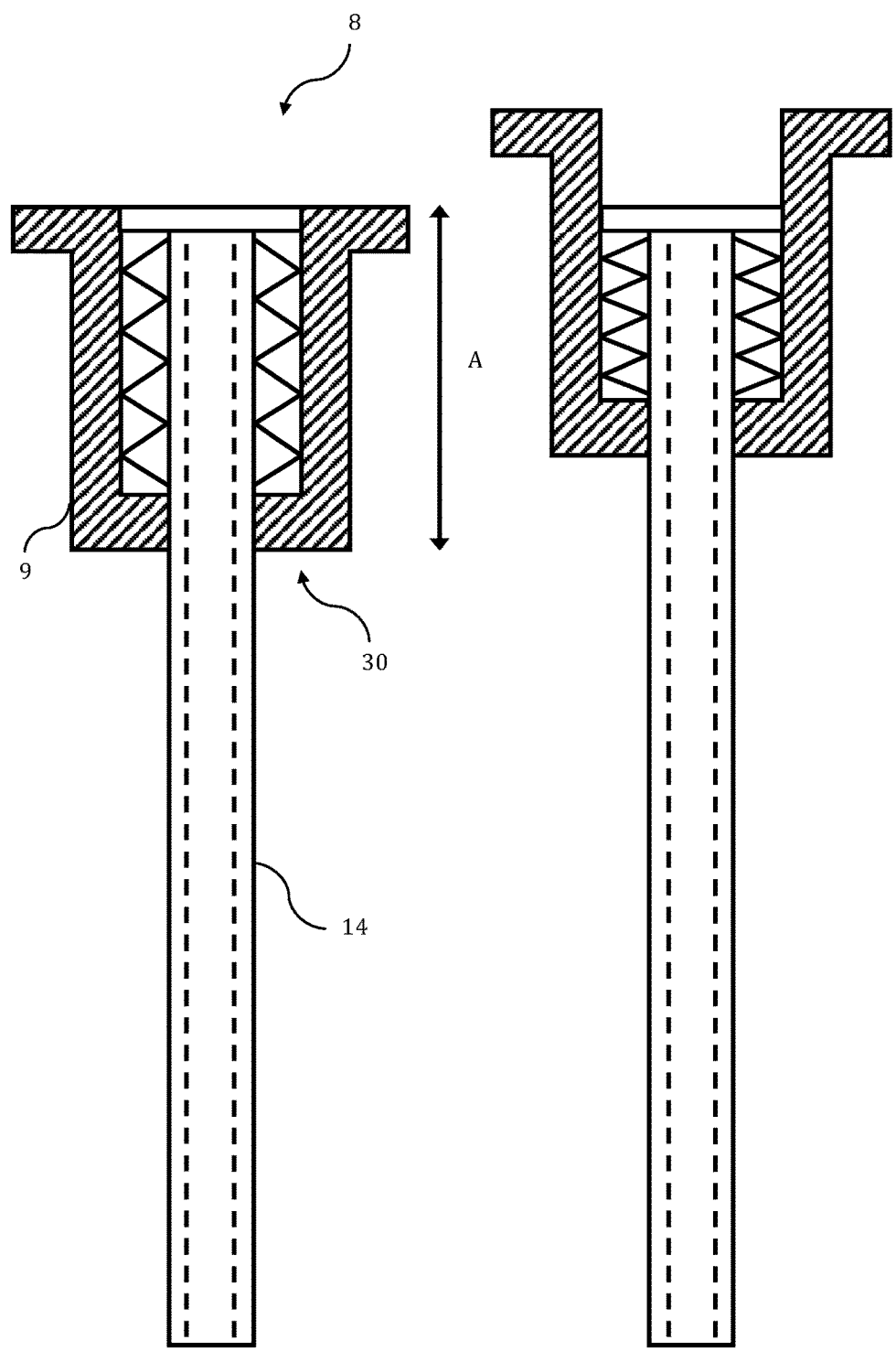
*FIG. 10A*        *FIG. 10B*

INTRAMEDULLARY RESECTION GUIDE AND METHODS

TECHNICAL FIELD

The present disclosure relates to bone cut positioning systems, and more specifically, to femoral bone cut positioning systems.

BACKGROUND

Orthopedic procedures for the replacement of all, or a portion of, a patient's joint typically require resecting (cutting) or reshaping the ends of the bones forming the joint. For example, total knee arthroplasty ("TKA") procedures typically include cutting open the knee, displacing the patella, resecting bone from the distal end of the femur, and resecting bone from the proximal end of the tibia to prepare the joint for prosthetic femoral and tibial implant components. Resecting the distal end of the femur often involves making one or more cuts including a planar distal cut. Resecting the proximal end of the tibia often involves making a planar proximal cut. In view of the foregoing surgical steps, TKA procedures are invasive but typically effective.

TKA procedures can be complicated by the fact that a mechanical axis of the leg does not typically line up with the anatomic axis or intramedullary canal. The mechanical axis includes a line from the center of a proximal joint to a distal joint of a long bone (e.g., femur or tibia), such that the mechanical axis is straight as it is a direct path between joint centers. The intramedullary generally follows the curvature of the femur, such that it is not straight as compared to mechanical axis.

Cut guides can be used to guide a saw and achieve the proper angle and position of the cuts performed during a TKA. Cut guides can be in the form of a guide member having slots therein for receiving and guiding the saw. In use, the guide member can be positioned against the bone with the assistance of positioning or alignment equipment. The proper positioning of such guide members is crucial to forming well-positioned bone cuts for attachment of the prosthetic femoral and tibial implant components. For example, the tibial cut affects spacing, alignment and balance between the tibia and femur when the knee is in flexion, and alignment and balance between the tibia and femur when the knee is in extension, as well as all points of articulation between extension and flexion. Once properly positioned and aligned, the guide member can be secured to the bone using bone pins or other securement means. For example, the guide member can be slidably mounted to an alignment guide, which can be mounted at an angle relative to an extramedullary guide or intramedullary rod. For an extramedullary tibial resection, an extramedullary guide can be located relative to the patient's anatomy to provide proper alignment relative to the tibia, and a guide member can be positioned on the proximal end of the tibia. Similarly, in an intramedullary tibial resection, an intramedullary rod can be inserted into a pre-drilled hole in the intramedullary canal of the tibia to provide anatomic alignment with a cut guide positioned on the proximal end of the tibia. For preparation of the femoral resection, an intramedullary rod can be positioned such that it extends across the distal end of the femur, and the cut guide can be positioned on the proximal end of the femur. The cut guide can be slid toward or away (medially-laterally) from the tibia or femur until it is properly positioned against the surface of the bone. The cut guide can then be secured to the bone with pins. The cut guide can be connected to the alignment guide using a pin/hole connect mechanism.

SUMMARY

To better illustrate the bone cut positioning system and related methods disclosed herein, a non-limiting list of examples is provided here:

In Example 1, a bone cut positioning system can comprise a positioning assembly. The positioning assembly can include a femoral attachment member configured to be fixed to a distal end of a femur, a light emitter mounting member configured to receive a light emitter, a channel configured to receive a depth selector slide, and a varus-valgus adjustment member configured to adjust a position of the positioning assembly relative to the femur to achieve a desired varus-valgus angle. A guide member can be removably coupled to the depth selector slide and configured to extend from the depth selector slide.

In Example 2, the bone cut positioning system of Example 1 is optionally configured such that the depth selector slide is magnetically coupled to the channel.

In Example 3, the bone cut positioning member of any one or any combination of Examples 1-2 is optionally configured such that the positioning assembly is manufactured of a biocompatible material.

In Example 4, the bone cut positioning system of any one or any combination of Examples 1-3 is optionally configured such that the femoral attachment member includes at least one pin aperture configured to receive a bone pin for securing the femoral attachment member to the distal end of the femur.

In Example 5, the bone cut positioning system of any one or any combination of Examples 1-4 is optionally configured such that the light emitter mounting member includes a light emitter receiving hole configured to receive at least a portion of the light emitter.

In Example 6, the bone cut positioning system of any one or any combination of Examples 1-5 is optionally configured to further comprise a magnetic interface for magnetically securing the light emitter to the light emitter mounting member.

In Example 7, the bone cut positioning system of any one or any combination of Examples 1-6 is optionally configured such that the light emitter is configured to magnetically power on when received by the light emitter mounting member.

In Example 8, the bone cut positioning system of any one or any combination of Examples 1-7 is optionally configured such that the light emitter includes a laser light emitter.

In Example 9, the bone cut positioning system of any one or any combination of Examples 1-8 is optionally configured such that the guide member is a single-use, disposable device.

In Example 10, the bone cut positioning system of any one or any combination of Examples 1-9 is optionally configured such that the positioning assembly is reusable.

In Example 11, the bone cut positioning system of any one or any combination of Examples 1-10 is optionally configured such that the varus-valgus adjustment member is rotatable relative to the femoral attachment member.

In Example 12, the bone cut positioning system of any one or any combination of Examples 1-11 is optionally configured such that the positioning assembly further includes a varus-valgus angle indicator configured to indicate a selected varus-valgus angle based on a position of the varus-valgus adjustment member.

In Example 13, the bone cut positioning system of any one or any combination of Examples 1-12 is optionally configured such that the positioning assembly further includes a plurality of ratchet teeth, the varus-valgus adjustment member configured to engage at least one of the ratchet teeth to maintain a desired position of the positioning assembly relative to the femur.

In Example 14, the bone cut positioning system of any one or any combination of Examples 1-13 is optionally configured such that the varus-valgus adjustment member includes a spring lockdown mechanism.

In Example 15, the bone cut positioning system of any one or any combination of Examples 1-14 is optionally configured such that the varus-valgus adjustment member includes an intramedullary rod aperture configured to receive an intramedullary rod.

In Example 16, the bone cut positioning system of any one or any combination of Examples 1-15 is optionally configured such that the positioning assembly further includes a depth indicator configured to indicate a position of the guide member relative to the channel.

In Example 17, a method for positioning a bone cutting guide on a femur can comprise inserting an intramedullary rod into an intramedullary canal of a femur and sliding a positioning assembly over the intramedullary rod. The positioning assembly can include a light emitter mounting member configured to receive a light emitter, a channel configured to receive a depth selector slide, and a ratcheted varus-valgus adjustment member configured to adjust a position of the positioning assembly relative to the femur, wherein the varus-valgus adjustment member is configured to receive the intramedullary rod. The method can further comprise contacting a femoral contact surface of the positioning assembly with a condylar surface of the femur, coupling the positioning assembly to the femur with at least one pin, attaching the bone cutting guide to the magnetic depth selector slide, attaching a light emitter to the light emitter mounting member, and coupling the bone cutting guide to the femur.

In Example 18, the method of Example 17 is optionally configured to further include adjusting the varus-valgus adjustment member to achieve a desired position of the positioning assembly relative to the femur.

In Example 19, the method of any one or any combination of Examples 17-18 is optionally configured to further include adjusting the depth selector slide to a specified resection level.

In Example 20, a bone cut positioning system can comprise a positioning assembly including a femoral attachment member configured to be fixed to a distal end of a femur and a light emitter mounting member configured to receive a light emitter, the light emitter configured to magnetically power on when received by the light emitter mounting member. A channel can be configured to receive a depth selector slide and a magnetic interface within the channel can be configured to magnetically secure the depth selector slide. A varus-valgus adjustment member can be configured to adjust a position of the positioning assembly relative to the femur to achieve a desired varus-valgus angle. The positioning assembly can include a plurality of ratchet teeth, and the varus-valgus adjustment member can be configured to engage at least one of the ratchet teeth to maintain a desired position of the positioning assembly relative to the femur. A guide member can be removably coupled to the depth selector slide and configured to extend from the depth selector slide.

In Example 21, the bone cut positioning system or method of any one or any combination of Examples 1-20 is optionally configured such that all elements or options recited are available to use or select from.

These and other examples and features of the present disclosure can provide the benefit of reducing errors that can occur from an intramedullary rod position. For example, even when the intramedullary rod is not positioned along the varus-valgus line of the femur, the varus-valgus adjustment member can correct for such errors and provide for a desired resection. Further benefits of the present disclosure can include a system or method of resecting a femur such that the amount of bone cut from the femur is substantially minimized. Benefits of the present disclosure can also include providing a resected fixation surface that provides an improved or more secure fit for TKA prosthetics, as compared to previous approaches.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 10A and 10B are partial section views depicting the example varus-valgus adjustment member of FIGS. 1 and 2.

DETAILED DESCRIPTION

The present disclosure describes a bone cut positioning system and related method of use. The bone cut positioning system and method can be used in various examples to enhance or facilitate a total knee arthroplasty (TKA) procedure, a partial knee arthroplasty procedure, or any other suitable knee surgery procedure in which one or more cuts are made on a femur, such as a distal end of the femur.

Generally, the examples described herein provide a means for positioning a bone cut on a femur. Although the following description focuses on TKA procedures, the described examples can also be used for partial knee arthroplasty procedures or other knee procedures in which femoral bone cuts are made.

Figure 1:
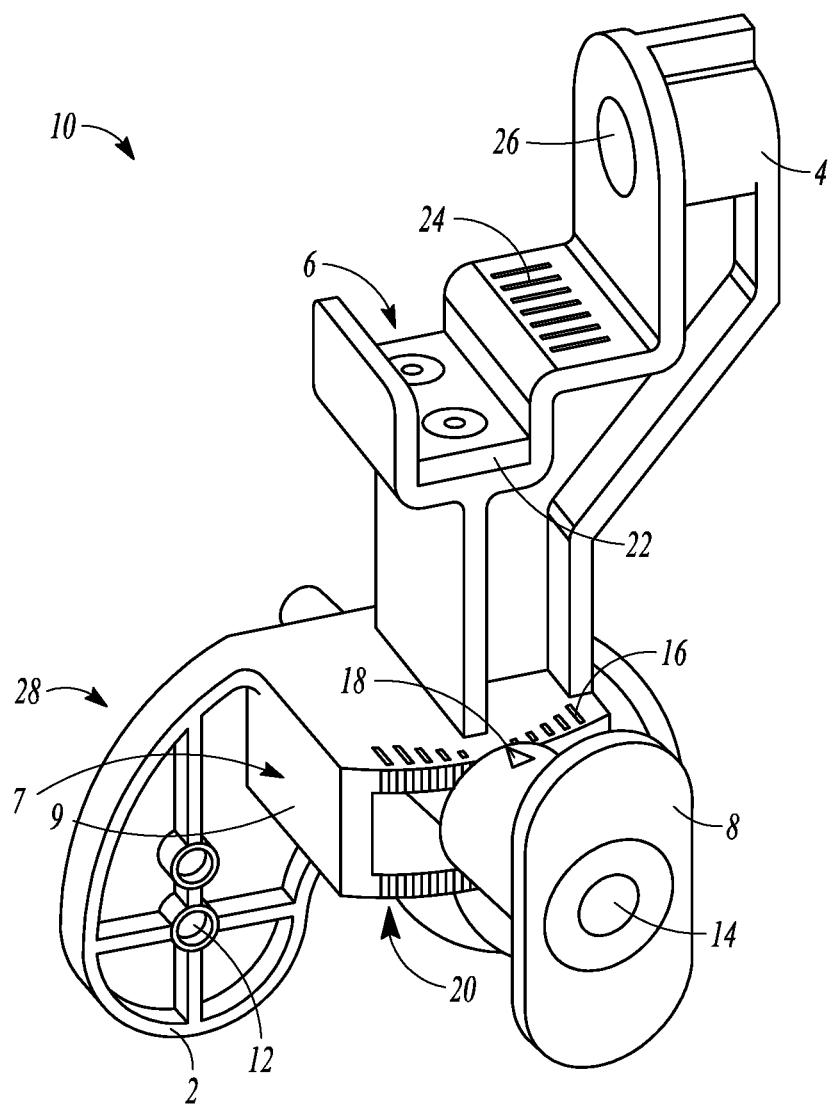
FIG. 1 is a perspective view of a bone cut positioning assembly, in accordance with at least one example.

FIG. 1. is a perspective view of a bone cut positioning assembly 10 in accordance with the present disclosure. One or more of the components of the bone cut positioning system 10 can be made of a biocompatible material, such as a material that does not produce a toxic, injurious, or immunological response in living tissue. Biocompatible materials can include, but are not limited to, ceramics, synthetic polymeric materials, and metallic materials such as titanium, a titanium alloy, cobalt chromium, cobalt chromium molybdenum, tantalum, or a tantalum alloy. In various examples, the bone cut positioning system 10 can be made of stainless steel. Furthermore, the bone cut positioning assembly 10 can be reusable, such as after sterilization. The bone cut positioning assembly 10 can be a component of the bone cut positioning system 11 (FIG. 3) as discussed herein.

As illustrated in FIG. 1, the bone cut positioning apparatus 10 can include a femoral attachment member 2 configured to be fixed to a distal end of a femur, a light emitter mounting member 4 including a light emitter receiving hole, a channel 6 configured to receive a depth selector slide, a magnetic interface 22, a varus-valgus adjustment member 8, a varus-valgus scale 16, a varus-valgus indicator, and a depth scale 24.

The femoral attachment member 2 can include a distal femoral contact surface 28 configured to contact the distal end of the femur. In various examples, the femoral attachment member 2 can include one or more pin apertures 12, with each pin aperture 12 being configured to receive a pin or other fastening member for securing the femoral attachment member 2 to the distal end of the femur. The one or more pin apertures 12 can be positioned on the femoral attachment member 2 to give a user options based on a geometry of the condyle. For example, one or more pins can be received by the one or more pin apertures 12 such a gap between the distal femoral contact surface 28 and the distal end of the femur is minimized.

The light emitter mounting member 4 can be configured to receive one or more light emitters. As illustrated in FIG. 1, the light emitter mounting member 4 can include a light emitter receiving hole 26 configured to receive at least a portion of a light emitter. The light emitter mounting member 4 can be disposed at any suitable position, such as above the femoral attachment member 2 when the femoral attachment member 2 is secured to the distal end of the femur. In an example, the light emitter mounting member 4 is configured such that the light emitter, when mounted, is substantially centered medially and laterally on the femur and perpendicular to a cutting plane, as described herein. Furthermore, the light emitter mounting member 4 can include a depth selector scale 24 configured to indicated a depth selection, as described herein.

As described above, the channel 6 can be configured to receive a depth selector slide. In an example, the channel 6 can include a magnetic interface 22 configured for magnetically securing the depth selector slide 32. That is, in various examples, the depth selector slide, as described herein, can be magnetically coupled to the channel 6. For example, magnetic interface 22 can removably retain the depth selector slide such that the depth selector slide can be moved within the channel 6 or removed from the channel 6.

The varus-valgus adjustment member 8 can be included in a varus-valgus assembly 7 including a base portion 9 connected to femoral attachment member 2 and operatively connected to varus-valgus adjustment member 8. The varus-valgus adjustment member 8 can be configured to adjust a position of the bone cut positioning system 10 relative to the femur to achieve a desired varus-valgus angle. In an example, the varus-valgus adjustment member 8 can be rotatable relative to an intramedullary rod, such as when the positioning assembly 10 has been slid on the intramedullary rod, as described herein. The varus-valgus adjustment member 8 can include a varus-valgus scale 16 and a varus-valgus indicator 18, as described herein. In various examples, the varus-valgus angle indicator 18 can be configured to indicate a selected varus-valgus angle based on a position of the varus-valgus adjustment member 8. The varus-valgus adjustment member 8 can include an intramedullary rod aperture 14 configured to receive an intramedullary rod. As described herein, the bone cut positioning system 10 can be configured to slide on an intramedullary rod inserted in a femoral canal and at least partially through the intramedullary rod aperture 14. As illustrated in FIG. 1, the base portion 9 of varus-valgus assembly 7 can include a plurality of ratchet teeth 20 configured such that engagement of the varus-valgus adjustment member 8 with at least one of the ratchet teeth 20 can maintain a desired position of the bone cut positioning assembly 10 relative to the femur, as described herein.

Figure 2:
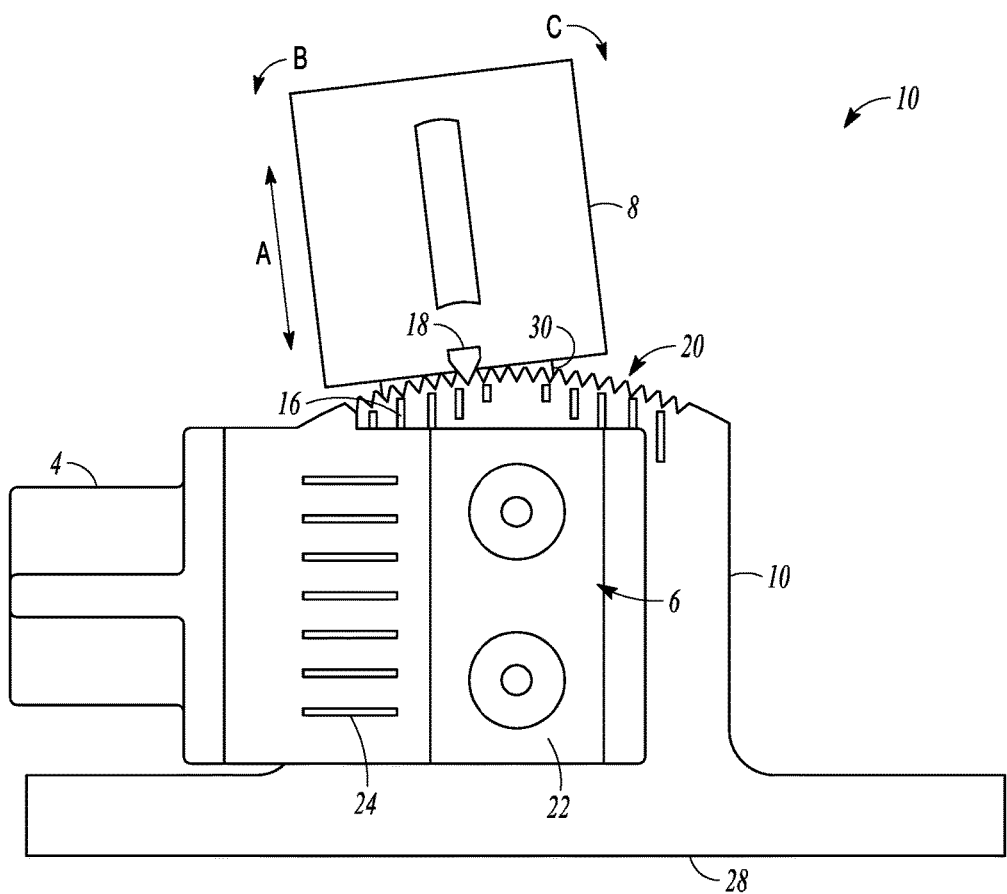
FIG. 2 is a top view of the bone cut positioning assembly, in accordance with at least one example.

FIG. 2 illustrates a top view of the bone cut positioning assembly 10. As shown, the varus-valgus adjustment member 8 can include a spring lockdown mechanism 30, configured such that the varus-valgus adjustment member 8 can be pulled in a direction A away from the ratchet teeth 20. When the varus-valgus adjustment member 8 is pulled in the direction A, the spring lockdown mechanism 30 can disengage the ratchet teeth 20 such that the varus-valgus adjustment member 8 can freely rotate in a direction B or a direction C. Rotation of the varus-valgus adjustment member 8 can adjust the position of the bone cut positioning assembly 10 and light emitter mounting member 4 relative to the femur or relative to the inserted intramedullary rod. In an example, the intramedullary rod aperture 14 of the varus-valgus adjustment member 8 can be slid over the intramedullary rod that has been inserted in a femoral canal. The varus-valgus adjustment member 8 can then be disengaged from the ratchet teeth 20 by pulling the varus-valgus adjustment member 8 in the direction A. Thereafter, the varus-valgus adjustment member 8 can be rotated in the directions B or C, such that the distal femoral contact surface 28 of the femoral attachment member 2 can be positioned parallel with the final bone-cut orientation according to the desired alignment, such as substantially flush with the distal end of the femur.

The varus-valgus adjustment member 8 can allow the user to select or adjust the positioning assembly 10 to a desired resection angle, such as based on pre-op X-rays or based on a light emitter 40, as described herein. In various examples, the distal femoral contact surface 28 of the femoral attachment member 2 can be positioned such that it forms an angle of about 1 degree, about 2 degrees, about 3 degrees, about 4 degrees, about 5 degrees, about 6 degrees, or about 7 degrees or more, with the distal end of the femur. When a desired varus-valgus position of the bone cut positioning assembly 10 has been selected, the varus-valgus adjustment member 8 can be pushed or allowed to return in the direction A toward the ratchet teeth 20, such that the varus-valgus adjustment member 8 engages at least one of the ratchet teeth 20. The position of the varus-valgus indicator 18 along the varus-valgus scale 16 can provide a visual indication of the selected varus-valgus position.

In an example, the varus-valgus adjustment member 8 can include one or more engagement members configured to engage or lock the varus-valgus adjustment member 8 with one or more of the ratchet teeth 20. In another example, the spring locking mechanism 30 can provide sufficient force to maintain contact between the varus-valgus adjustment member 8 and one or more of the ratchet teeth 20. In various embodiments the spring locking mechanism 30 can provide sufficient force maintain a position of the varus-valgus adjustment relative to the femoral attachment member 2 or the distal end of the femur.

Figure 3:
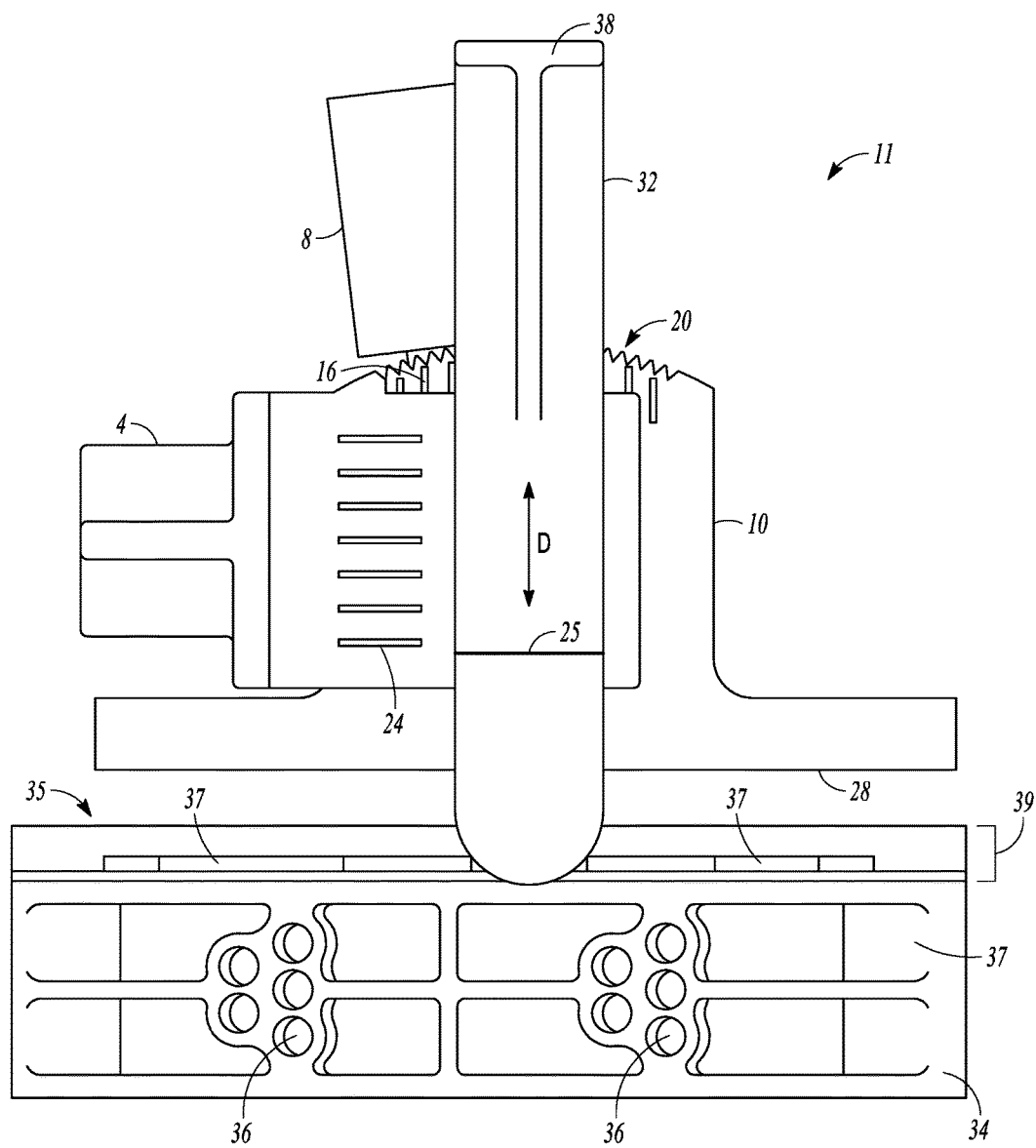
FIG. 3 is a top view of the bone cut positioning system including a guide member, in accordance with at least one example.

FIG. 3 is a top view of the bone cut positioning system 11 which includes the bone cut positioning assembly 10 engaged with a depth selector slide 32 for a guide member 34. In various examples, the guide member 34 can be removably coupled to the depth selector slide 32, such that the guide member 34 extends from an end portion of the depth selector slide 32. The guide member 34 can include a cut guide having at least one of a cutting surface 35 and a cutting slot 37 configured for guiding a saw or other cutting instrument. The guide member can be a single-use, disposable device manufactured from a biocompatible material as described herein. As illustrated in FIG. 3, at least a portion of the biocompatible material forming the guide member 34 can be a resorbable material, such as the portion 39 of the guide member 34 that includes the cutting surface 35 and the cutting slots 37. A resorbable material can include a material capable of being absorbed into tissue of a human subject upon separation of the material from the guide member 34. For example, the resorbable material can include a poly-L-lactide, a poly-D-lactide, a poly-DL-lactide, a ployglycolide, a polycaprolactone, or a combination thereof. In an example, the resorbable material portion 39 of the guide member 34 can be removable or replaceable, such that the guide member 34 can be reused after sterilization and replacement of the portion 39.

The guide member 34 can include one or more guide member apertures 36 configured to receive a pin or other fastening member. The pin or fastening member can be insertable into the guide member aperture 36 and can be configured to secure the guide member 34 to the femur. In various examples, the guide member 34 can be removably coupled to the depth selector slide 32, such as by a clip, a quick release mechanism, a hinge, a magnet, a friction plate, or any other suitable connection mechanism.

The depth selector slide 32 can include a grip 38 configured for allowing a user to move the depth selector slide 32 within the channel 6 (see FIG. 1) in a direction D. The depth selector slide 32 can include a magnetic surface configured to contact or be positioned sufficiently close to the magnetic interface 22 (see FIG. 1) such that the depth selector 32 can be retained within the channel 6. The magnetic force between the magnet of the depth selector slide 32 and the magnetic interface 22 can be strong enough to temporarily fix the depth selector slide 32 within the channel 6, but weak enough such that a user can reposition or remove the depth selector slide 32 from the bone cut positioning assembly 10 by pushing, pulling, or lifting the depth selector slide 32. In various examples, the depth selector slide 32 can include a depth indicator 25, such that the depth of the guide member 34 can be discerned by the location of the depth indicator 25 relative to the depth scale 24.

Figure 4:
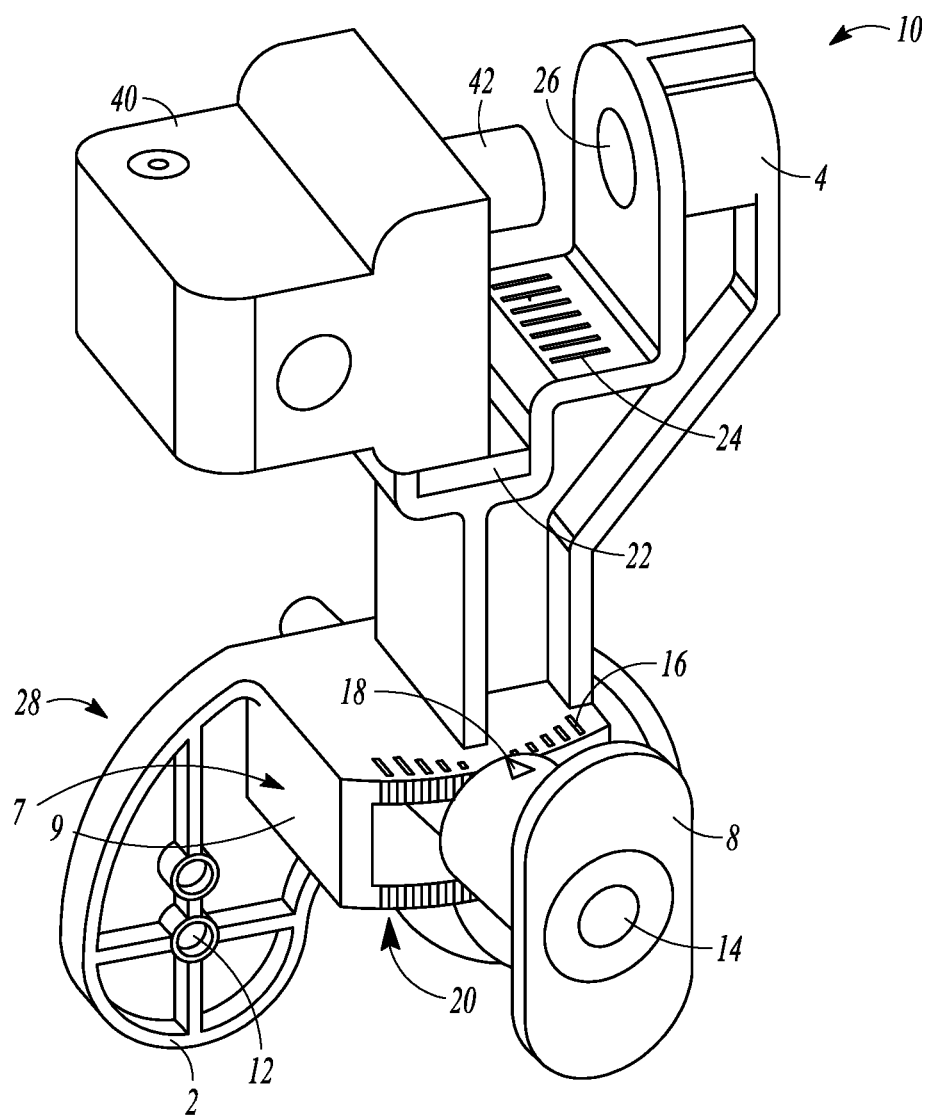
FIG. 4 is an alternate perspective view of the bone cut positioning assembly and a light emitter, in accordance with at least one example.

FIG. 4 is a perspective view of the bone cut positioning assembly 10 and a light emitter 40. The light emitter 40 can generally include a light source configured to emit a light beam, as described herein. A light source can include, for example, a light emitting diode, a laser, or a combination thereof. The light emitter 40 can include a light emitter protrusion 42 configured to be received by the light emitter receiving hole 26 of the light emitter mounting member 4. Although the light emitter protrusion 42 is shown as cylindrical, it can be any three-dimensional geometric shape capable of being received within the light emitter receiving hole 26. Thus, the light emitter receiving hole 26 and the light emitter protrusion 42 can be defined by a similar three-dimensional shape, or non-similar three-dimensional shapes that allow for engagement between the light emitter protrusion 42 and the light emitter receiving hole 26.

The light emitter 40 can be configured to emit a light upon being coupled to the light emitter mounting member 4. For example, the lighter emitter 40 can include a magnetic switch that activates or powers on the light source upon being coupled to the light emitter mounting member 4. Alternatively or in addition, the light emitter 40 can include a manual on/off switch. Alternatively, the light emitter 40 can be fixed, such as an integral assembly, with the positioning assembly 10.

Figure 5:
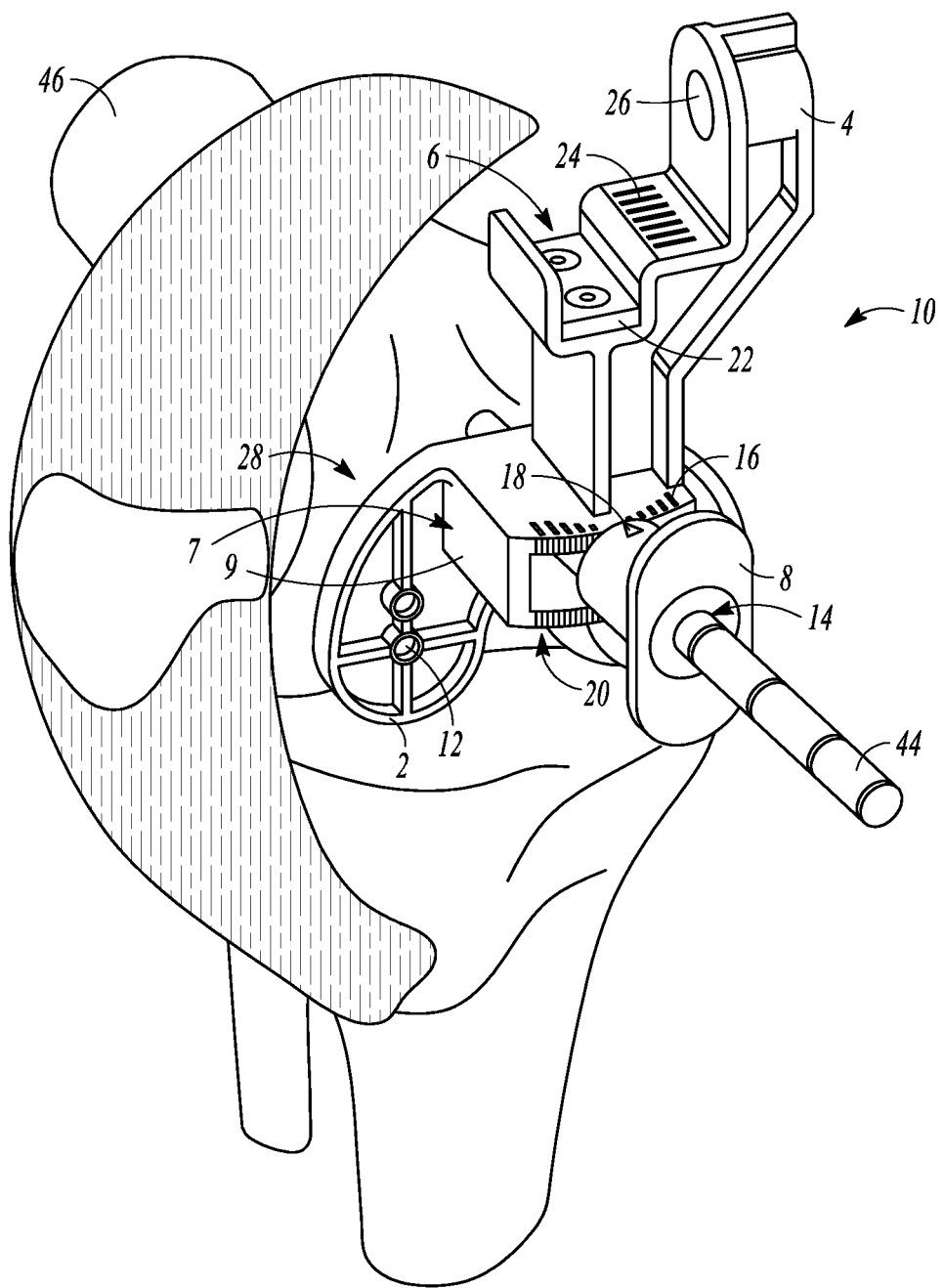
FIG. 5 is a perspective view of the bone cut positioning assembly engaged with a femur, in accordance with at least one example.

FIG. 5 is a perspective view of the bone cut positioning assembly 10 engaged with a femur 46. As shown, the intramedullary rod aperture 14 of the varus-valgus adjustment member 8 can be slid onto an intramedullary rod 44 that has been inserted into a femoral canal of the femur 46. Prior to engaging the bone cut positioning assembly 10 with the intramedullary rod 44, the patella 49 can be moved out of the way of the distal end of the femur 46 such that the femoral contact surface 28 can contact the femur 46. As shown in FIG. 5, the varus-valgus adjustment member 8 can be adjusted, as described herein, while on the intramedullary rod 44 according to pre-op X-rays or the light emitter. In an example, the varus-valgus adjustment member 8 can adjust the positioning assembly 10 such that only one side of the distal contact surface 28 is in contact with, and pinned to, the condyle.

Figure 6:
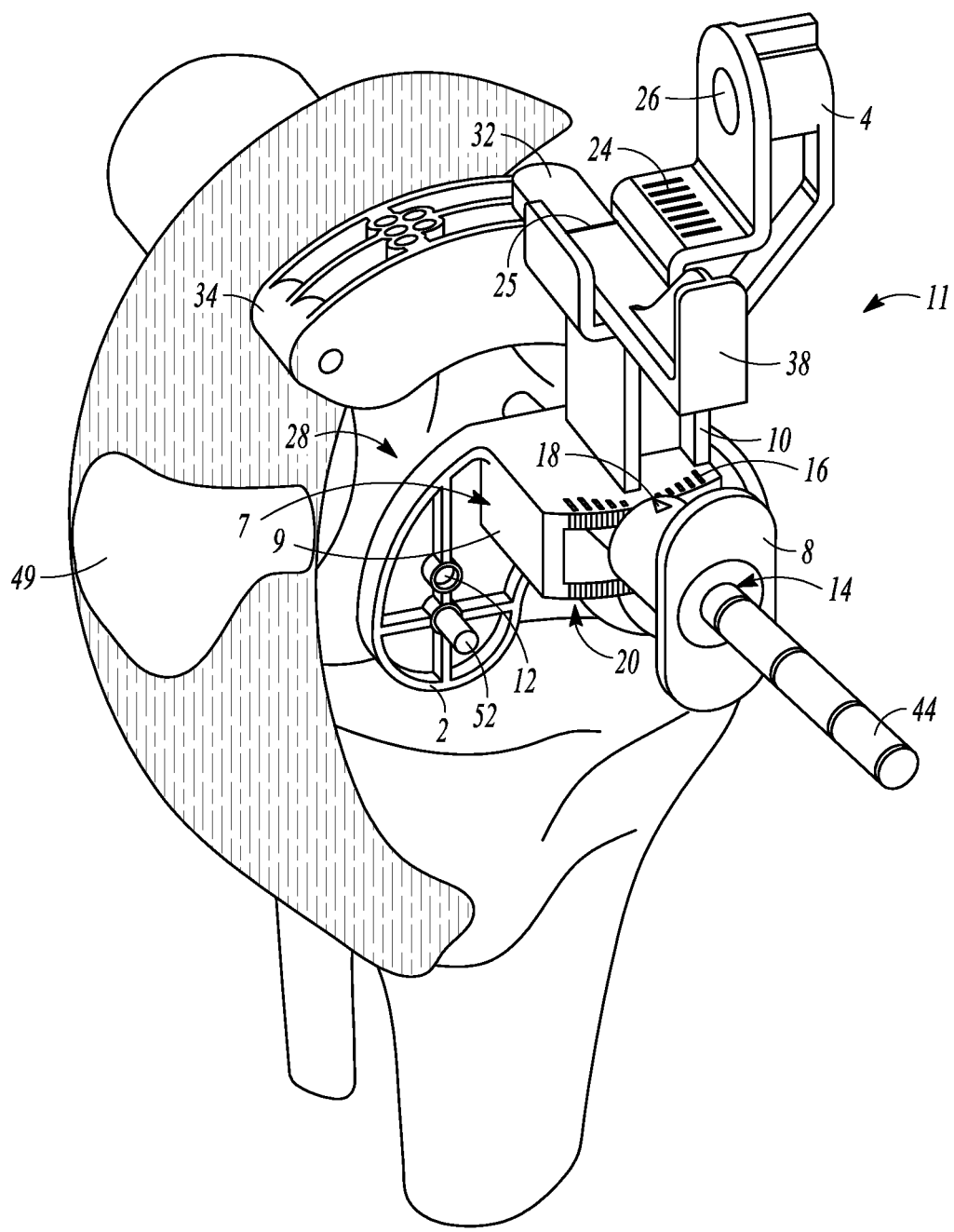
FIG. 6 is an alternate perspective view of the bone cut positioning system including the guide member positioned adjacent to a femur, in accordance with at least one example.

FIG. 6 is a perspective view of the bone cut positioning system 11 including the bone cut positioning assembly 10 coupled with the guide member 34 engaged with the femur 46. The femoral attachment member 2 can be secured to the femur 46 by one or more pins 52. As illustrated in FIG. 6, it may not be necessary to insert a pin 52 into each of the apertures 12 to sufficiently secure the femoral attachment member 2 to the femur 46. The depth selector slide 32 can be moved such that the attached guide member 34, when secured to the femur 46, will provide a desired resection depth.

Figure 7:
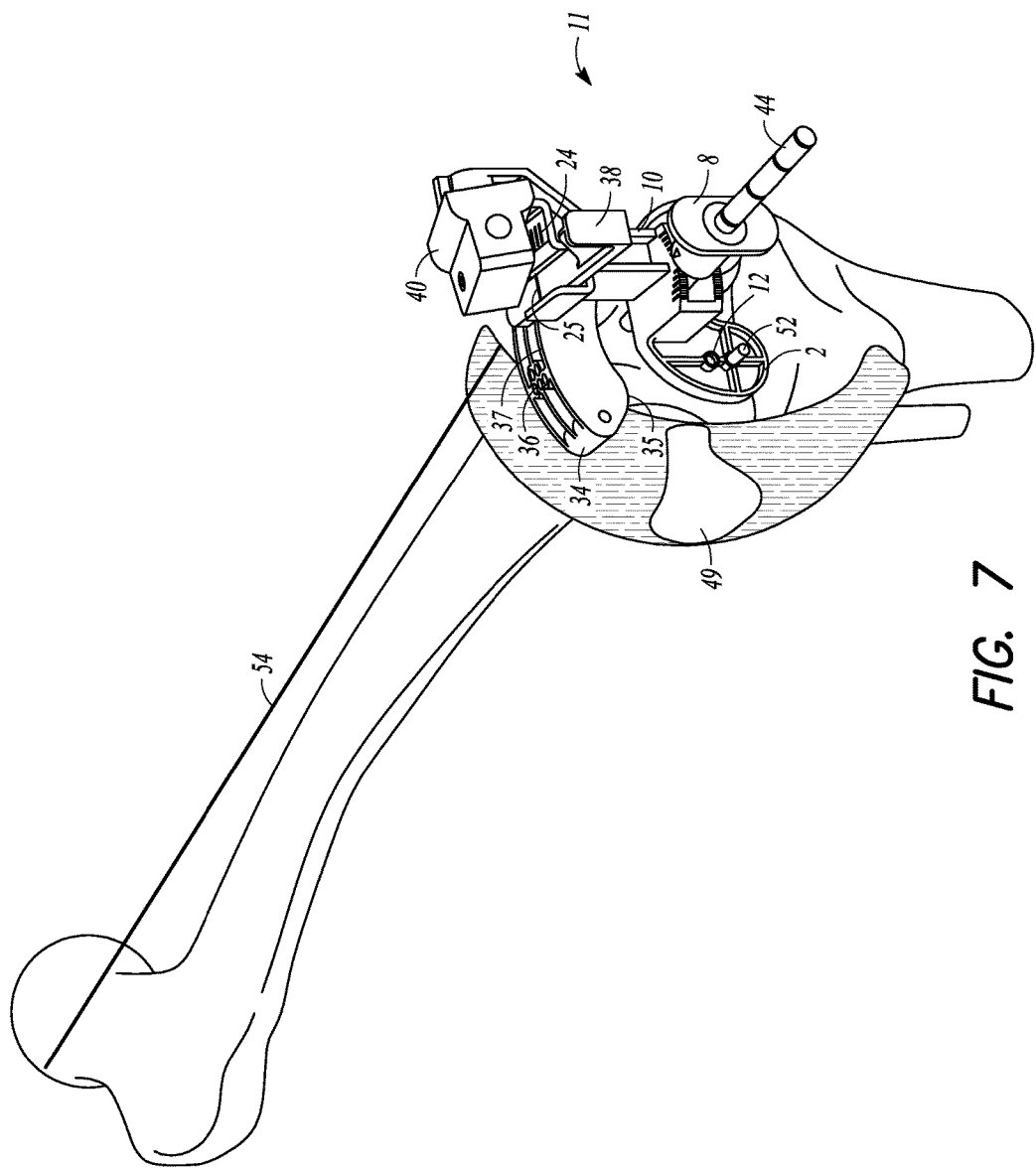
FIG. 7 is a perspective view of the bone cut positioning system including, the light emitter, and the guide member positioned adjacent to a femur, in accordance with at least one example.

FIG. 7 is an alternate perspective view of the bone cut positioning system 11 including the bone cut positioning assembly 10 engaged with the femur 46, and further illustrating the positioning of the guide member 34 and the light emitter 40. As shown in FIG. 7, the light emitter 40 can emit a plane of light 54 that extends longitudinally along at least a portion of the femur 46. More specifically, the light emitter 40 can direct the plane of light 54 toward a surface of the femur 46 for guiding orientation or adjustment of the bone cut positioning system 11. In various examples, the plane of light 54 can include a beam, a cross, a fan, or any other suitable light configuration. The plane of light 54 can be used by the user to select or adjust the varus-valgus adjustment member 8 after the positioning assembly 10 has been slid onto the intramedullary rod 44, but prior to inserting the one or more pins 52. The engagement between the lighter emitter 40 and the light emitter mounting member 4, as discussed above, can be configured to allow tilting of the light emitter 40 by the user to allow adjustment of the plane of light 54 along the femur 46 to confirm the mechanical axis or other desired alignment with respect to the patient anatomy. In various examples, at least one of the cutting surface 35 and cutting slots 37 can be oriented along a plane that is substantially perpendicular to the plane of light 54.

Figure 8:
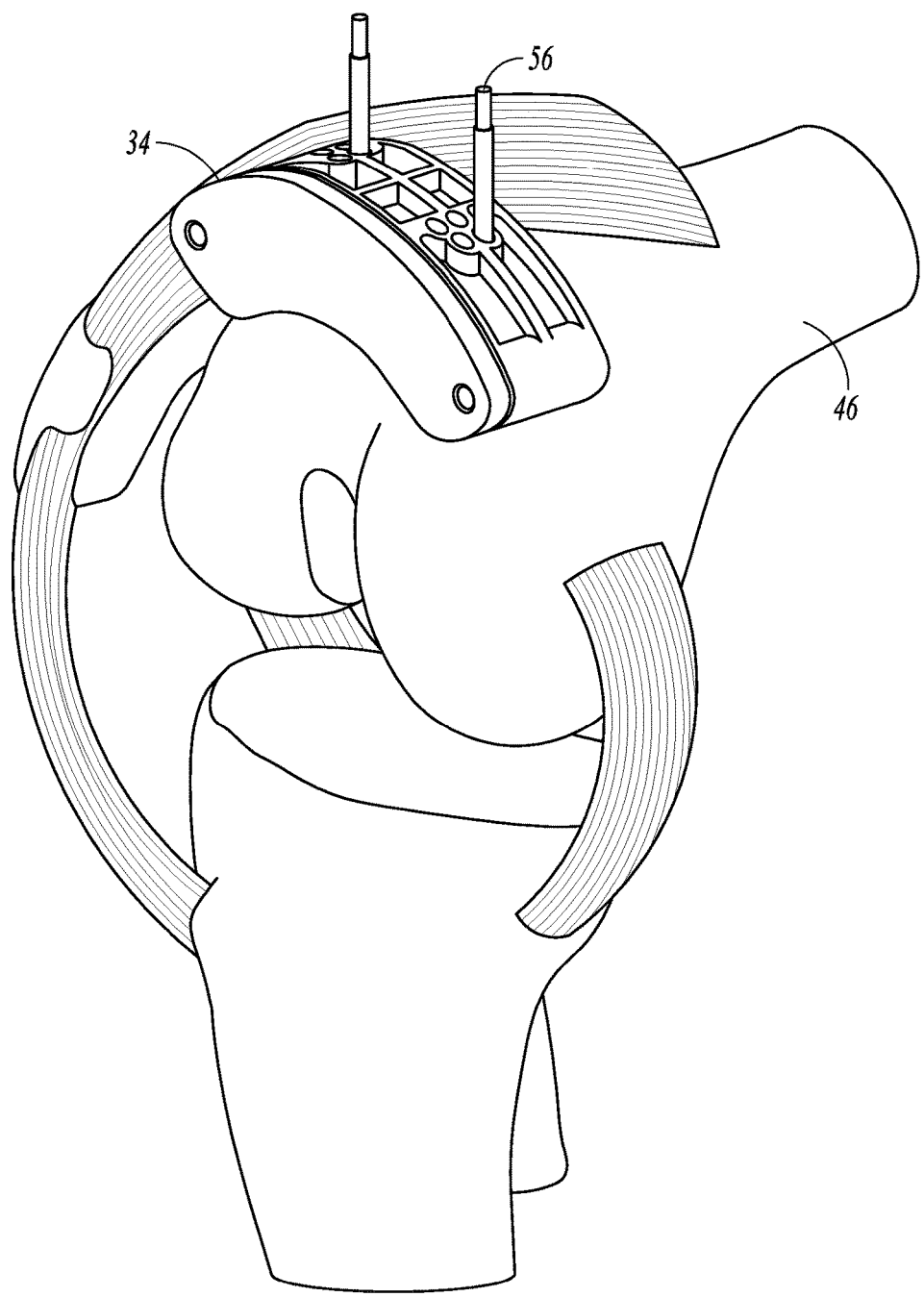
FIG. 8 is a perspective view of the guide member mounted on the femur, in accordance with at least one example.

FIG. 8 is a perspective view of the guide member 34 mounted on the femur 46 after the bone cut positioning system 11 has been removed from the femur 46. In view of the foregoing description, the bone cut positioning system 11 can be adjusted, such as by the varus-valgus adjustment member 8 and the depth selector slide 32, to position the guide member 34 in a desired position on the femur 46. Once the desired position of the guide member 34 has been obtained, one or more pins 56 can be inserted into one or more guide member apertures 36 in the guide member 34 to secure the guide member 34 to the femur 46. The guide member 34 can then be detached from the depth selector slide 32, and the one or more pins 52 in the femoral attachment member 2 can be removed to allow the bone cut positioning system 11 to be slid off the intramedullary rod 44. At such point, the guide member 34 of FIG. 8 can be used to guide one or more cut of the distal end of the femur 46.

Figure 9:
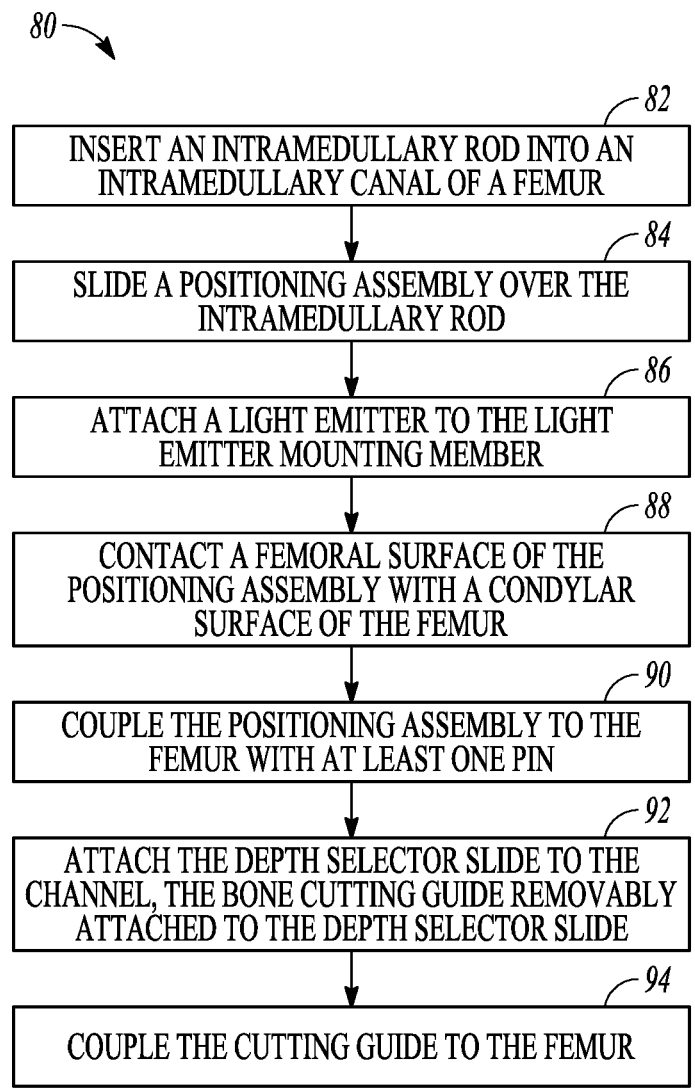
FIG. 9 is a method for positioning a bone cutting guide member on a femur, in accordance with at least one example.

FIG. 9 is a method 80 for positioning a bone cutting guide on a femur. The method 80 can include inserting 82 an intramedullary rod into an intramedullary canal of a femur. Further, the method 80 can include sliding 84 a bone cut positioning system over or onto the intramedullary rod. The bone cut positioning system can include a light emitter mounting member configured to receive a light emitter, a channel configured to receive a depth selector slide, and a ratcheted varus-valgus adjustment member configured to adjust a position of the bone cut positioning system or assembly relative to the femur. The varus-valgus adjustment member can include an aperture configured to receive the intramedullary rod.

In various examples, the method 80 can also include adjusting the bone cut positioning apparatus in a varus-valgus orientation relative to the femur. For example, the varus-valgus adjustment member can be adjusted to achieve a desired varus-valgus angle of the bone cut positioning system relative to the intramedullary rod. Further, the desired varus-valgus angle can be based on pre-operative X-rays or based on a user preference. In various examples, before or after adjusting the varus-valgus adjustment member, but after sliding the bone cut positioning system onto the intramedullary rod, the method can include attaching 86 a light emitter to the light emitter mounting member. Attaching the light emitter can include activating a light source, such as magnetically or by an on/off switch. Adjusting the varus-valgus orientation of the bone cut positioning system can include moving or tilting a light beam emitted by the light emitter to shine along approximately the mechanical axis or other chosen anatomical alignment axis of the femur. In addition to further adjusting varus-valgus angle, the light beam emitted by the light emitter can be used to confirm the desired angle selected the user or based on pre-operative X-rays.

The method 80 can include contacting 88 a femoral contact surface of the bone cut positioning assembly with a condylar surface of the femur. Further, the method 80 can include coupling 90 the bone cut positioning assembly to the femur with one or more pins or fastening members, so as to secure at least on side of the bone cut positioning assembly to the femur. The depth selector slide can be attached 92 to the channel, with the bone cutting guide removably attached to the depth selector slide. The method 80 can further include coupling 94 the bone cutting guide to the femur.

In various examples, the method can include adjusting the depth selector slide to a specified or desired resection level of the distal end of the femur. The method can include, after coupling the bone cutting guide to the femur, detaching the bone cutting guide from the depth selector slide. Further, the method can include removing the one or more pins or fastening members securing the femoral attachment member to the femur and sliding the bone cut positioning system off of the intramedullary rod. Further, the method can include removing the intramedullary rod from the femoral condyle and resecting the distal end of the femur.

FIGS. 10A and 10B are partial section views depicting a portion of varus-valgus adjustment member 8 of FIGS. 1 and 2. Varus-valgus adjustment member 8 includes a spring lockdown mechanism 30, an example of which is illustrated in FIGS. 10A and 10B. Varus-valgus adjustment member 8 can include a handle 9 and receive intramedullary rod aperture/sleeve 14. A bone cut positioning system in accordance with this application, for example, system 10 of FIG. 1 can slide onto an intramedullary rod inserted in the femoral canal and at least partially through aperture 14. FIGS. 10A and 10B illustrate adjustment of varus-valgus adjustment member 8. For example, handle 9 of varus-valgus adjustment member 8 can be pulled in direction A out of engagement with, for example, ratchet teeth associated with the bone cut positioning system. When the varus-valgus adjustment member 8 is pulled in the direction A, the spring lockdown mechanism 30 can disengage, for example, the ratchet teeth 20 (shown in FIGS. 1 and 2) such that the varus-valgus adjustment member 8 can be freely adjusted.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other embodiments can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A bone cut positioning system, comprising:
   a positioning assembly configured to be inserted onto an intramedullary rod disposed in an intramedullary canal of the femur, the positioning assembly including:
   a femoral attachment member comprising a femoral contact surface and configured to be fixed to a distal end of a femur;
   a varus-valgus adjustment member coupled and rotatable relative to the femoral attachment member, the varus-valgus adjustment member being configured to receive the intramedullary rod and to adjust a position of the positioning assembly relative to the femur to achieve a desired varus-valgus angle;
   a ratchet mechanism coupled to the femoral attachment member and configured to lock the bone cut positioning system at the desired varus-valgus angle;
   a light emitter mounting member coupled to the femoral attachment member and configured to receive a light emitter;
   a depth selector slide received within a channel of the light emitter mounting member; and
   a guide member removably coupled to the depth selector slide and configured to extend from the depth selector slide.

2. The bone cut positioning system of claim 1, wherein the depth selector slide is configured to be magnetically coupled to the channel.

3. The bone cut positioning system of claim 1, wherein the positioning assembly is manufactured from at least one biocompatible material.

4. The bone cut positioning system of claim 1, wherein the femoral attachment member includes at least one pin aperture configured to receive a pin for securing the femoral attachment member to the distal end of the femur.

5. The bone cut positioning system of claim 1, wherein the light emitter mounting member includes a light emitter receiving aperture configured to receive at least a portion of the light emitter.

6. The bone cut positioning system of claim 5, further including the light emitter and a magnetic interface for magnetically securing the light emitter to the light emitter mounting member.

7. The bone cut positioning system of claim 6, wherein the light emitter comprises a magnetic switch that is configured to be activated to power on the light emitter when received by the light emitter mounting member.

8. The bone cut positioning system of claim 1, further including the light emitter, and wherein the light emitter includes a laser light emitter.

9. The bone cut positioning system of claim 1, wherein the guide member is a single-use, disposable device.

10. The bone cut positioning system of claim 1, wherein the positioning assembly is reusable.

11. The bone cut positioning system of claim 1, wherein the positioning assembly further includes a varus-valgus angle indicator configured to indicate a selected varus-valgus angle based on a position of the varus-valgus adjustment member.

12. The bone cut positioning system of claim 1, wherein the varus-valgus adjustment member and the ratchet mechanism are included in a varus-valgus assembly, the ratchet mechanism including a plurality of ratchet teeth, and the varus-valgus adjustment member configured to engage at least one of the ratchet teeth to maintain a desired position of the positioning assembly relative to the femur.

13. The bone cut positioning system of claim 1, wherein the ratchet mechanism includes a spring-loaded ratchet mechanism.

14. The bone cut positioning system of claim 1, wherein the varus-valgus adjustment member includes an intramedullary rod aperture configured to receive the intramedullary rod.

15. The bone cut positioning system of claim 1, wherein the positioning assembly further includes a depth indicator configured to indicate a position of the guide member relative to the channel.

16. A bone cut positioning system configured to be inserted onto an intramedullary rod disposed in an intramedullary canal of the femur, comprising:
   a femoral attachment member comprising a femoral contact surface and configured to be fixed to a distal end of a femur;
   a varus-valgus assembly comprising a base coupled to the femoral attachment member and a varus-valgus adjustment member rotatable relative to the base and the femoral attachment member, the varus-valgus adjustment member configured to receive the intramedullary rod and to adjust a position of the bone cut positioning system relative to the femur to achieve a desired varus-valgus angle;
   a ratchet mechanism coupled to the femoral attachment member and configured to lock the bone cut positioning system at the desired varus-valgus angle;
   a light emitter mounting member coupled to the base and receiving a light emitter, the light emitter comprising a magnetic switch that is configured to be activated to power on the light emitter when received by the light emitter mounting member;
   a depth selector slide received within a channel of the light emitter mounting member;
   a magnetic interface within the channel configured to magnetically secure the depth selector slide; and
   a cut guide member removably coupled to the depth selector slide and configured to extend from an end of the depth selector slide, the cut guide member including at least one cutting surface and one or more cutting slots.

17. A method for positioning a bone cutting guide on a femur, comprising:
inserting an intramedullary rod into an intramedullary canal of the femur;
sliding a positioning assembly over the intramedullary rod, the positioning assembly including;
a light emitter mounting member configured to receive a light emitter;
a depth selector slide configured to be received within a channel of the light emitter mounting member; and
a ratcheted varus-valgus adjustment member configured to adjust a position of the positioning assembly relative to the femur, wherein the varus-valgus adjustment member is configured to receive the intramedullary rod;
attaching the light emitter to the light emitter mounting member;
contacting a femoral contact surface of the positioning assembly with a condylar surface of the femur;
coupling the positioning assembly to the femur with at least one pin;
attaching the depth selector slide to the channel, the bone cutting guide removably attached to the depth selector slide; and
coupling the bone cutting guide to the femur.

18. The method of claim 17, further including adjusting the varus-valgus adjustment member, prior to coupling the positioning assembly to achieve a desired position of the positioning assembly relative to the femur.

19. The method of claim 17, further including adjusting the depth selector slide to a desired resection level.

* * * * *